United States Patent [19]
Winder et al.

[11] Patent Number: 5,520,612
[45] Date of Patent: May 28, 1996

[54] ACOUSTIC SYSTEM FOR BONE-FRACTURE THERAPY

[75] Inventors: Alan A. Winder, Westport, Conn.; Roger J. Talish; John P. Ryaby, both of West Caldwell, N.J.

[73] Assignee: Exogen, Inc., West Caldwell, N.J.

[21] Appl. No.: 367,471

[22] Filed: Dec. 30, 1994

[51] Int. Cl.⁶ ........................................ A61N 7/00
[52] U.S. Cl. .......................... 601/2; 128/660.03; 607/51
[58] Field of Search ................................ 607/51; 601/2; 128/660.03, 739, 740

[56] References Cited

U.S. PATENT DOCUMENTS

| | | | |
|---|---|---|---|
| 4,530,360 | 7/1985 | Duarte | 607/51 |
| 4,905,671 | 3/1990 | Senge et al. | 601/2 |
| 4,979,501 | 12/1990 | Valchanov et al. | 601/2 |
| 5,211,160 | 5/1993 | Talish et al. | 607/51 |
| 5,393,296 | 2/1995 | Rattner | 607/51 |
| 5,409,446 | 4/1995 | Rattner | 601/4 |

*Primary Examiner*—Ruth S. Smith
*Assistant Examiner*—Brian L. Casler
*Attorney, Agent, or Firm*—Hopgood, Calimafde, Kalil & Judlowe

[57] ABSTRACT

A transducer for non-invasive transcutaneous transmission of pulsed ultrahigh-frequency acoustic radiation, in body tissue and/or fluids adjacent a bone fracture is "on target" when a fraction of the propagated energy within the longitudinal-response lobe of the transducer encounters a crack or other open feature of the fracture, where a gap or space exists between closely spaced fracture walls. The ultrahigh-frequency acoustic radiation sees this "on target" feature as the entrance to a waveguide, whereby pulsed ultrahigh-frequency acoustic radiation is guided within the crack. When this acoustic radiation encounters a gap of at least a quarter wavelength (at the ultrahigh frequency), a standing wave condition establishes itself, with dissipation of the ultrahigh frequency and with demodulation to establish a therapeutically beneficial low-frequency acoustic condition, within the fracture, and acting where most needed, namely, on and between wall regions of adjacent fragments of the broken bone. Collagen, callus and cartilage development is accelerated, closing the gap in a matter of days, so that thereafter zone-flooding of shear waves from transducer radiation can be osteogenically operative upon both bone fragments of the fracture and on the collagen through which they are united at first tentatively and then increasingly more securely as treatment continues, from day to day, as with one or more single treatments of 20 minutes per day.

47 Claims, 3 Drawing Sheets

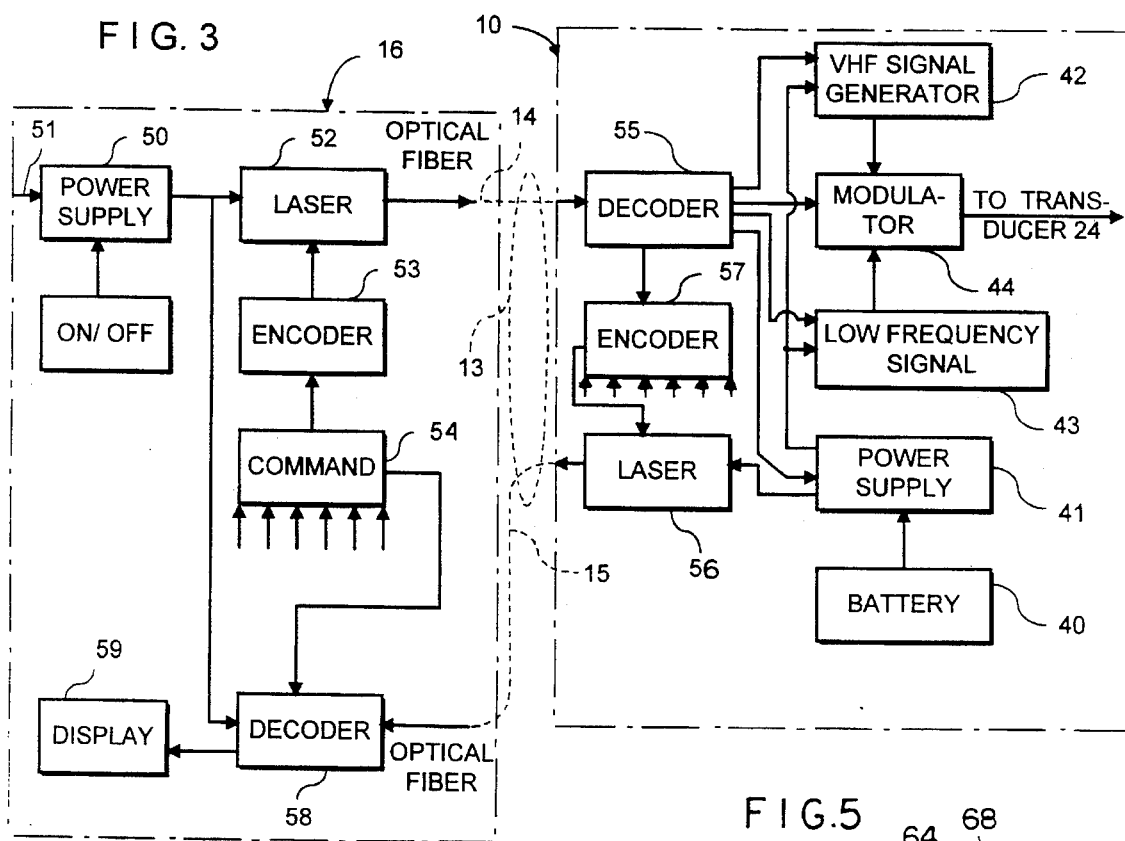
FIG. 3
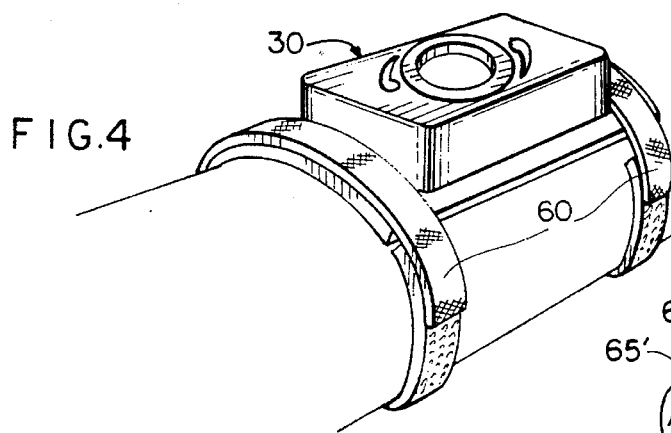
FIG. 4
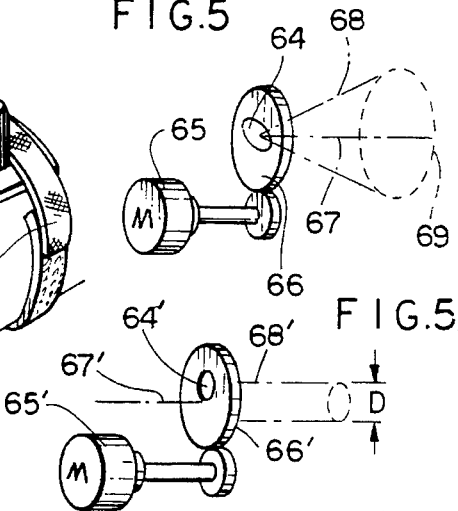
FIG. 5
FIG. 5A
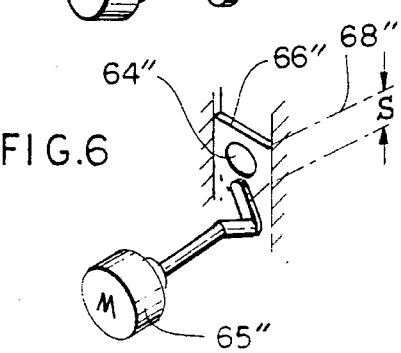
FIG. 6
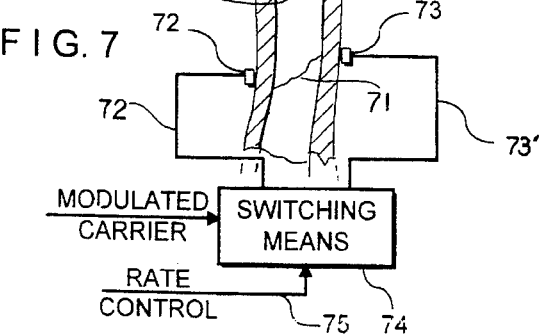
FIG. 7

FIG. 8
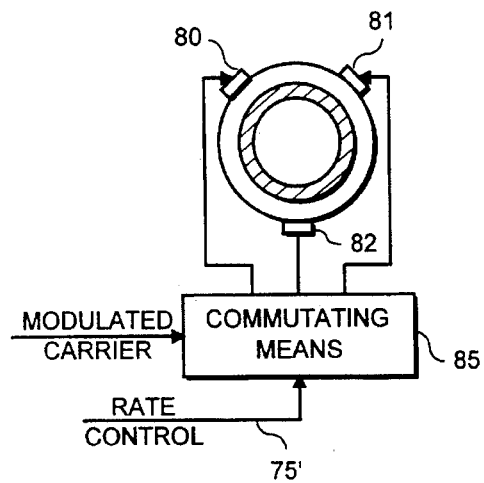
FIG. 12
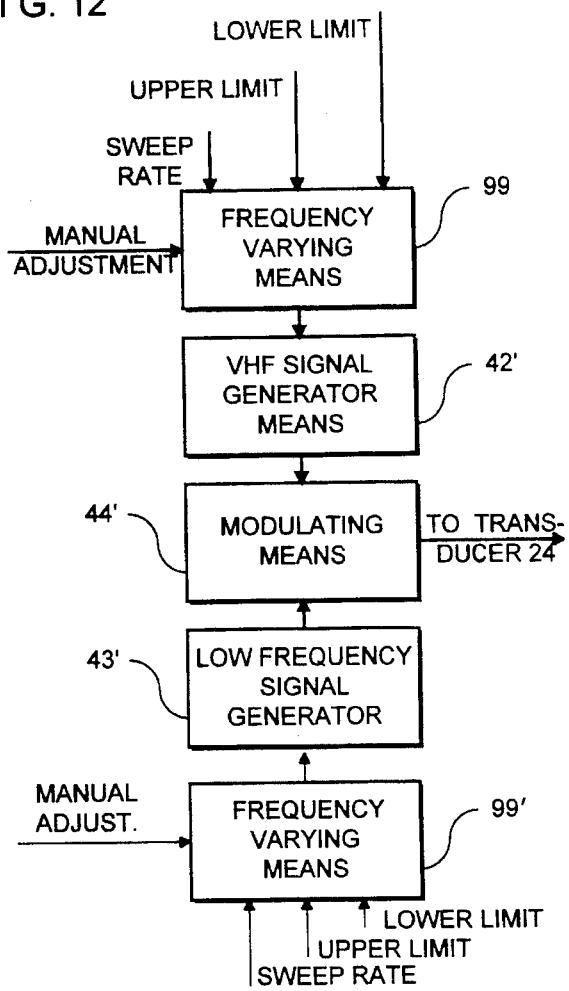
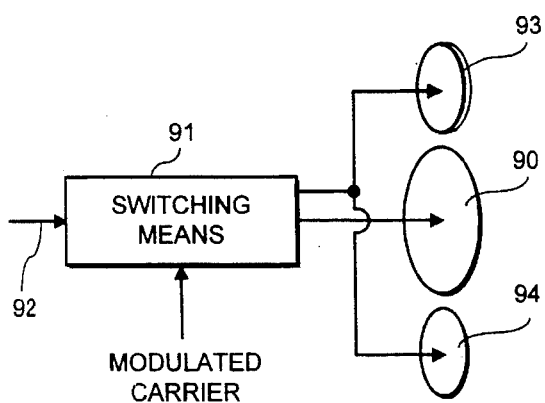
FIG. 9
FIG. 10
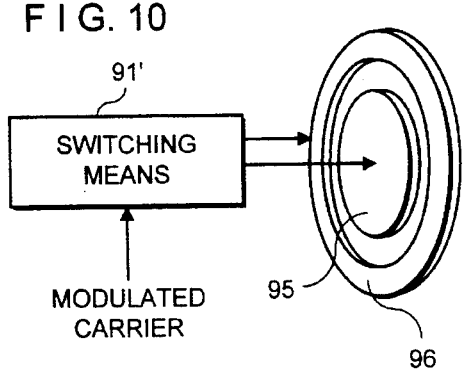
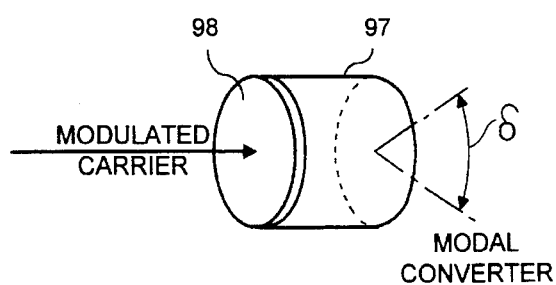
FIG. 11

1

ACOUSTIC SYSTEM FOR BONE-FRACTURE THERAPY

BACKGROUND OF THE INVENTION

The invention relates to use of ultrasonic radiation at relatively low levels into living tissue, for the surgically non-invasive healing treatment of bone fractures.

Duarte U.S. Pat. No. 4,530,360 describes a technique of treating bone defects, such as bone fractures, pseud-arthroses and the like, using a pulsed radio-frequency ultrasonic signal applied via a transducer to the skin of the patient and directing sound waves to the bone defect to be healed. Duarte's teaching is said to proceed from the fact that bone is piezoelectric in nature; instead of inducing a current which promotes bone growth with an external electromagnetic field, or generating such a current directly, the mechanical energy of Duarte's ultrasound is converted to an electric current in the bone, to then and thereby promote healing.

Talish et al. U.S. Pat. Nos. 5,003,965 and 5,186,162 advance the Duarte technique by providing features which favor safety in the patient's periodic use of pulsed ultrahigh frequency acoustic delivery to an afflicted region of the patient's body, by electrically separating a power-supply and pulse generating module from a local low-power radio-frequency generator. The local radio-frequency generator, complete with battery, is contained in a miniaturized enclosure, which also mounts piezoelectric transducer means for patient-operated application to a special mounting fitment that is stabilized by the fixation cast for the patient's damaged limb; and pulse-modulation of local high-frequency output to the transducer is via an optical-fiber link between the power supply/pulse-generating module and the miniaturized enclosure (and its transducer).

The osteogenic properties of Duarte's pulsed ultrahigh-frequency acoustic therapy have been confirmed by others, but it can be said that for the most part these others are non-specific in recommendations for how and where to apply such acoustic therapy with respect to the known fracture location. At least, two German practitioners* are specific in their recommendation that the directional axis of the acoustic signal should be normal to the bone, and at an offsetting longitudinal distance of approximately two inches from the fracture, it being noted that the Knoch/Klug energy level may cause tissue damage if directed at the situs of the fracture.

*H.-G. Knoch and W. Klug, "Stimulation of Fracture Healing with Ultrasound, Springer-Verlag, Berlin, Heidelberg 1990 (translation).

The present invention proceeds from an awareness that a relatively low-frequency (e.g. 5 Hz to 10 kHz) and low-intensity (e.g. less than 100 milliwatts/cm$^2$) acoustic signal has probably the greatest value and effectiveness for osteogenic therapy, but conventional wisdom must concede that such a signal, non-invasively delivered to the body, stands little chance of being therapeutically delivered to a fractured situs. And even if the fractured bone is the tibia, fractured at the skin, and therefore as close as possible for non-invasive access, there is no assurance that the region of confronting separation of bone fragments will receive the low-frequency excitation which is believed to be necessary for initial generation of collagen and callus formation, to close the space or spaces between bone fragments which confront each other across a separating space or gap.

BRIEF STATEMENT OF THE INVENTION

It is an object of the invention to provide an improved technique and apparatus for the surgically non-invasive utilization of ultrahigh-frequency acoustic energy in the acceleration of bone-fracture repair.

It is a specific object to surgically non-invasively utilize confronting surfaces of separated bone fragments in the local detection of a low-frequency signal of osteogenic value, at and within the situs of a bone fracture.

A general object is to achieve the above objects with equipment which is safe and simple for patient use, and which involves only minimum change of existing equipment.

In its presently preferred embodiment, the invention achieves these objects by providing an ultrahigh-frequency carrier signal for low-power excitation of an acoustic transducer that is acoustically coupled to a limb or other part of a living body, for surgically non-invasive transcutaneous delivery of acoustic energy to body tissue and/or fluids adjacent at least a portion of a bone fracture, wherein the fracture is at least in part characterized by a space between confronting surfaces of the fracture; for example, the acoustic transducer has a radiating frontal-surface area which propagates a primary directional lobe of acoustic energy in body tissue and/or fluids about a central or longitudinal axis, and this primary directional lobe is concentrically surrounded by primary shearwave lobes of acoustic energy. The carrier frequency is sufficiently elevated to establish a standing-wave condition in one or more spaces between confronting surfaces of a bone fracture, as long as the space is dimensionally characterized by at least a quarter-wavelength at the carrier frequency, thereby enabling demodulation of the carrier at the situs of the fracture. Generally speaking, the lower limit of confronting fragment separation in a bone fracture is in the order of 0.04 or 0.05 mm, and a bone disorder of lesser separation is generally indicative as a stress fracture. Preferably, a low-frequency signal that is present as a modulation on the carrier is the product of such demodulation and is thus directly available for its therapeutic value where most needed, in and around space within the fracture. Within a matter of days, healing proceeds at an accelerated pace in the environment of such demodulation, with resultant collagen, callus and cartilage development in reduction of the space, to the point of dimensional insufficiency for standing-wave development; but the pattern of carrier wave propagation in body tissue and/or fluids surrounding the central axis of acoustic propagation is rich in therapeutically beneficial shear waves of acoustic energy, flooding a region which surrounds the fracture. Fracture-healing therapy may continue with the same or with suitably modified acoustic propagation at and around the fracture site. Various specific embodiments are described for bone-repair treatment of the character indicated, suitably for one or more single approximately 20-minute treatments per day.

BRIEF DESCRIPTION OF THE DRAWINGS

The invention will be described in detail, in conjunction with the accompanying drawings in which:

FIG. 3 is a simplified block diagram of components of the remote-control system of FIGS. 1 and 2;

FIG. 4 is a view in perspective to show a modified application of an embedment fixture as in FIG. 2, but adapted for strapped application to an otherwise fixated limb, e.g. fixated by an external fixator (not shown);

FIG. 5 is a schematic diagram to illustrate a conical mode of acoustically scanning the region of a bone fracture;

FIG. 5A is a diagram as in FIG. 5 to illustrate a cylindrical mode of acoustic scanning;

FIG. 6 is another diagram as in FIG. 5 to illustrate a reciprocating lineal mode of acoustic scanning;

FIG. 7 is a schematic diagram to show coordinated use of two transducers in treatment of a bone fracture;

FIG. 8 is a diagram as in FIG. 7 to illustrate coordinated use of a greater plurality of transducers;

FIG. 9 is a diagram to illustrate use of a plurality of transducers in a linear array;

FIG. 10 is a view as in FIG. 9 to illustrate use of a plurality of transducers in concentric array;

FIG. 11 is a simplified diagram to illustrate use of a modal converter as part of a phase of fracture repair, with the invention; and FIG. 12 is a block diagram to illustrate certain selectively available features pertaining to use of the invention.

DETAILED DESCRIPTION

Figure 1:
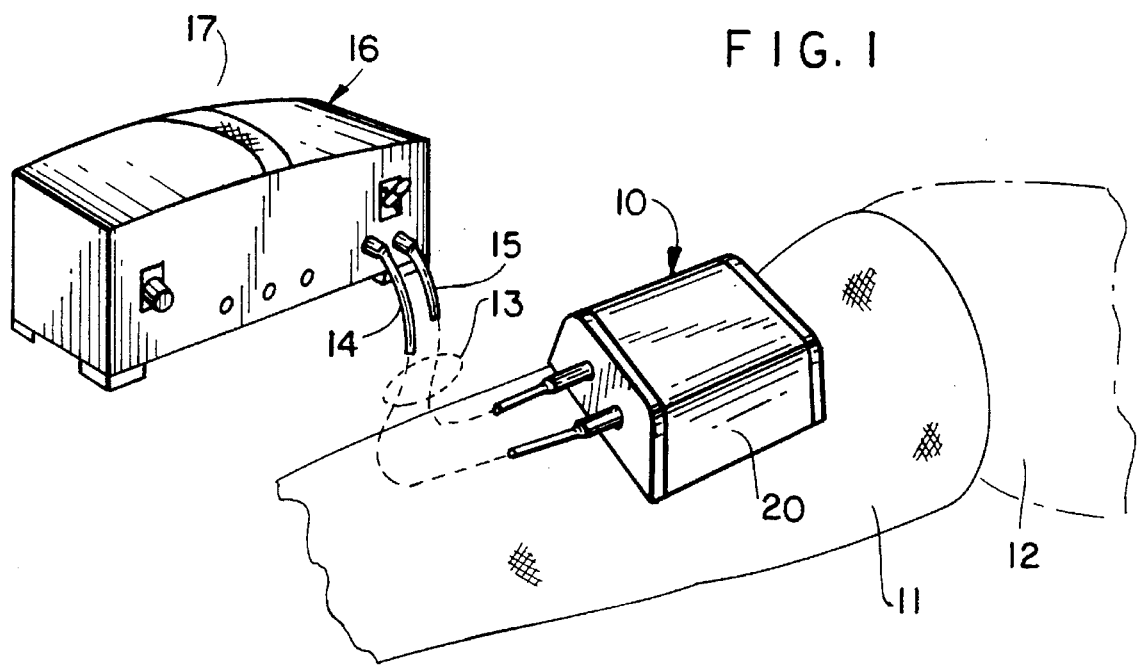
FIG. 1 is a simple perspective view of remote-control and body-applicator units of the invention, in the context of fixedly orienting the body-applicator unit for accelerated repair of a fractured tibia that is fixated in a cast.
Figure 2:
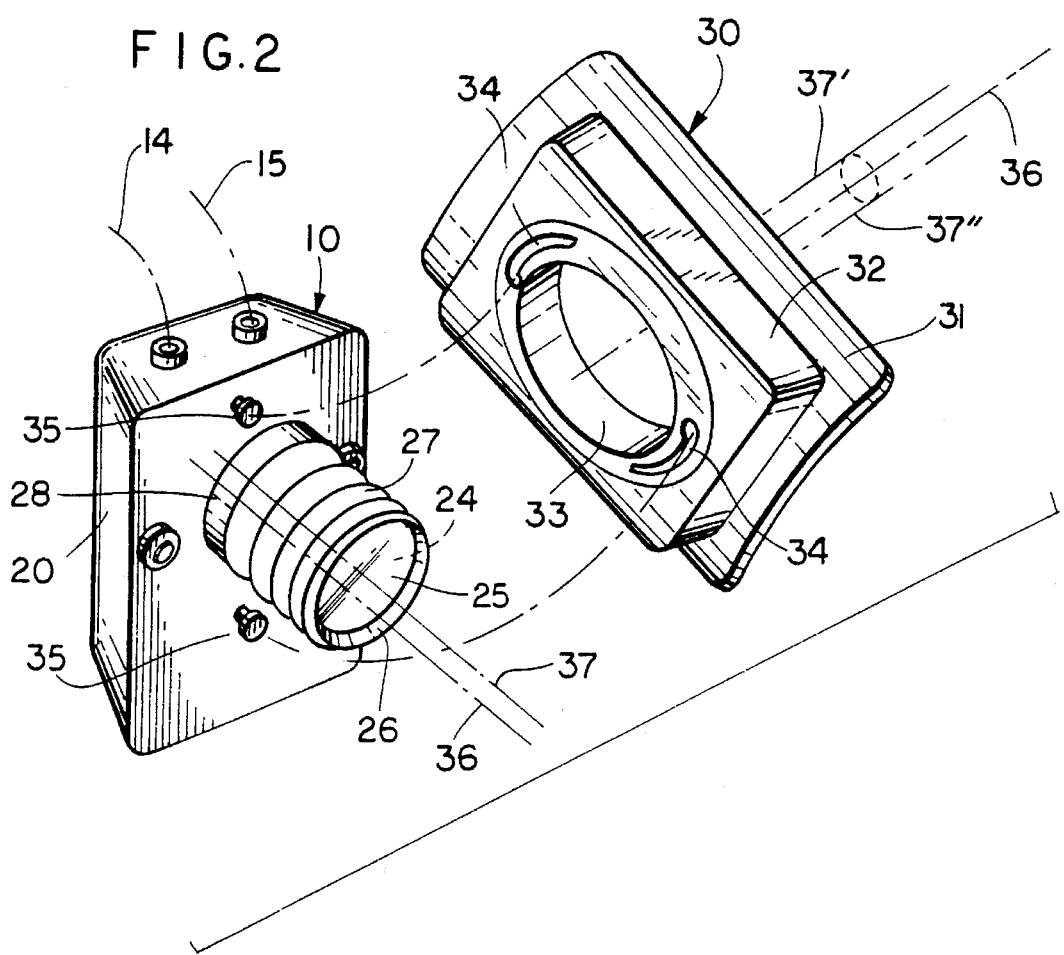
FIG. 2 is an enlarged view in a first perspective of the body-applicator unit of FIG. 1 and in an image-reversed second perspective of an embedment fixture for embedment in the cast of FIG. 1, wherein the fixture is adapted for detachably mounted reception of the body-applicator unit.

Referring initially to FIGS. 1 and 2, the invention is illustratively shown to utilize basic components resembling those described in said U.S. Pat. No. 5,186,162 which patent is hereby incorporated by reference. It suffices here to identify in these drawings a body-applicator unit 10, shown mounted to an orthopedic cast 11 for treatment of a bone fracture, such as a tibia fracture in a human leg 12. A flexible cable 13 comprising separately sheathed fiber-optic lines 14, 15 connects the body-applicator unit 10 to a remote-control unit 16, which may be relatively compact and portable, as suggested by a carrying handle 17; and detachable connectors of optical-transmission lines 14, 15 plug into the front panel of control unit 16.

The electrical contents, within housing 20 of the body-applicator unit 10, may be generally as described in detail in said U.S. Pat. No. 5,003,965, but with important differences to be indicated below. It suffices to state that housing 20 contains storage batteries and circuity of oscillator/driver components (sometimes referred to as the ultrasonic generator), with flexible lead connection to a thin flat transducer element 24. Element 24 is suitably a commercially available piezoelectric disc, as of the lead-zirconium-titanate material known as PZT-4; and element 24 will be understood to include a separate foil electrode bonded to each of its front and back surfaces, to enable thickness fluctuation in response to driven excitation. Transducer 24 is coated with an outer impedance-matching layer 25 of epoxy and is otherwise part of a sealed component 26 that is secured to the outer end of a sylphon-type bellows 27, of molded softly compliant elastomeric material. The base end 28 of bellows 27 is clamped to the front panel of housing 20, around an opening (not shown) for transducer-lead connection to the output of electric-component circuitry within the housing.

FIG. 2 further shows a mounting fixture 30 which can be fixed or otherwise secured to the patient and which serves for removable mounting of the treatment head 10. As shown, the fixture 30 comprises a light-weight outer generally rectangular frame having a peripheral flange 31 which, in the case of an orthopedic cast 11, will be understood to be embedded in hardened material of the cast. Within the confines of flange 31, upstanding body structure 32 has a central opening which provides rotational support for a ring member 33 having a pair of diametrically opposite arcuate slot formations 34 which are adapted for removably engaged retention of the treatment head, via mounting studs 35 which extend from the front panel of the treatment head 10. Headed ends of studs 35 will be understood to be enterable into enlarged ends of the slot formations 34, and treatment head 10 becomes frictionally or otherwise secured to the mounting fixture 30, upon partial bayonet-like rotation of head 10 with respect to ring 33.

As will later become clear, it is a feature of the invention that, with treatment head 10 thus secured to a rotatable part of the fixture 30, a central axis 36 of adjustable treatment-head rotation is defined for the mounted head 10, but the front panel of housing 20 positions the transducer axis 36 of rotational adjustment of the mounted treatment head. Therefore, rotary adjustment of the treatment head about axis 37 will dictate an eccentrically gyrated orbital displacement of the central longitudinal-response axis 37 of transducer 25 about the rotary adjustment axis 36. In FIG. 2, limits of this gyrated displacement of the transducer axis 37 are shown at 37', 37".

It has been indicated generally above that it is important to the invention that the ultrahigh-frequency signal with which transducer 24 is driven shall be so elevated as to be able to establish a standing-wave condition in body tissue and/or fluids in the space between fragments of a broken bone. Such a space will be at least 0.04 mm for the case of a bone fracture; anything less than substantially 0.04 mm will be generally indicative of a stress fracture, and greater space between bone fragments will be generally indicative of physical breakage of bone structure. For a standing-wave condition, the space must be sufficient to the extent of at least one-quarter wavelength at the frequency of the excitation signal; for example, in body tissues and/or fluids, and for a space of 0.04 mm or 0.05 mm, the ultrahigh frequency must be at least ten megahertz (10 MHz) in order to establish a standing-wave condition between adjacent surfaces of adjacent bone fragments. However, larger spaces between confronting surfaces of fractured bone can be much greater than 0.04 mm. Therefore, our preferred range of ultrahigh-frequency signal to the transducer will be in the range up to at least 10 MHz, at which frequency a quarter wavelength for a standing-wave condition is 0.04 mm.

In the simplified block diagram of FIG. 3, the body-applicator unit 10 is fully self-contained in the sense that it includes its own power source at battery 40, and power-supply means 41 for operation of an ultrahigh-frequency generator 42 and for operation of a low-frequency signal generator 43, which is suitably and preferably a pulse generator having a low-frequency pulse-repetition rate. A modulator 44 connected to generators 42, 43 supplies pulse-modulated ultrahigh-frequency signals to the transducer 24 which, through the interposition of a coupling gel, transmits pulse-modulated acoustic signals to the region of a fractured bone; illustratively, the coupling gel may be the filling of a pillow or envelope of flexible plastic which is transparent to the acoustic transmission.

It will be understood that all necessary settings within the described components of the body-applicator unit may serve all needed therapeutic operations, with merely an on/off switch as the single externally operated control. However, for safety purposes and for greater opportunity to change and monitor certain variables, such tasks are in FIG. 3 relegated to the remote-control unit 16, with reliance on optical-fiber lines 14, 15 for control and monitoring of the applicator unit 10. Alternatively, for the case of a battery-operated remote unit 16, electric-wire cable control of a body-applicator unit 10 is desirable.

In FIG. 3, the remote-control unit 16 has a power supply 50 which relies upon a house-current connection 41, and which powers laser means 52 coupled to optical fiber 14, subject to digital codification at 53 pursuant to instructions from a command module 54 which includes a microcomputer. At the receiving end of optical fiber 14, a decoder 55 sorts out various instructions to components of the body-applicator unit. The body-applicator unit is further shown with its own battery-powered laser means 56, and a plurality of arrows to an encoder 57 will be understood to indicate that a plurality of individual "report-back" connections (not shown) are also provided, for monitoring purposes, to the operative modular components of body applicator 10. All monitoring data reported to and encoded at 57 becomes digitally transmitted by laser means 56 and transmitted by the other optical fiber 15, back to the remote-control unit 16 where it is decoded at 58 for display at 59.

FIG. 4 is a simplified view in perspective to illustrate that the mounting fixture 30 of FIG. 2 may also be adjustably mounted to a human body part, via adjustable strap means 60, retained by hook-and-loop fastener means, it being understood that protective gauze or flannelette (not shown) between the body part and the individual straps is recommended to avoid chafing any skin. An arrangement as in FIG. 4 will be seen to serve a patient who relies upon external fixation (not shown) between bone screws (also not shown) which need present no interference with the strap-mounted assembly shown.

FIG. 5 is a schematic diagram to show that the modulated ultrahigh-frequency acoustic signal transmitted by a transducer (64) and body-coupled via a suitable gel, may be mechanically displaced in a conically orbiting scan motion, pursuant to slow drive by motor means 65. As shown, transducer 64 is mounted to a disc 66 which is motor-driven about an axis 67, and transducer 64 is tilt-mounted to disc 66 such that its central axis 68 of acoustic propagation is at an acute angle to the axis 67 of rotation. Rotation via motor 65, with edge-drive connection to disc 66, thus produces an eccentrically gyrated conical scan of the fracture site, as suggested at 69.

In the arrangement of FIG. 5A, corresponding parts identified in FIG. 5 are given the same reference numbers, with primed notation. The only difference in FIG. 5A is that transducer 64' is mounted to disk 66' such that its central axis 68' of acoustic propagation is parallel to but radially offset from the rotary axis 67' of disc 66'. The result is to have the transducer propagate over a cylindrically gyrated course, with resultant circular acoustic scan at diameter D, for the central axis of transducer propagation.

In the arrangement of FIG. 6, a transducer 64" is mounted to a plate 66" which is slidably guided for recycled straight-line displacement of its central axis 68" of acoustic propagation between rectilineal scan limits that are separated to the extent S. A motor 65" drives a crank-and-link connection to plate 66" to account for the recycled displacement.

The schematic diagram of FIG. 7, in connection with a bone 70 that is fractured at 71 along a course which has both transverse and longitudinal components illustrates that in certain instances, it may be desirable and therapeutically more effective to mount two transducers 72, 73 as in accordance with the technique described in connection with FIG. 4, at each of two locations, namely at substantially diametrically opposite sides of the fracture and at longitudinally offset locations which generally lap the respective ends of the course of the fracture. In such event, switching means 74 will be understood to commutate modulated ultrahigh-frequency carrier in alternation to the respective transducers 72, 73, via lines 72', 73'. An additional connection 75 to means 74 will be understood to suggest selective control of the rate of alternation, varying say, on the one hand, from one low-frequency pulse modulation (in line 72') to the next (in line 73'); or to one burst of pulse modulations in line 72', and to a similar but succeeding burst of pulse modulations in line 73'; or further to a manually remote control of which transducer is to be driven, alone or in alternation with the other transducer.

The arrangement schematically depicted in FIG. 8 illustrate a plurality of three like transducers 80, 81, 82 mounted, as by strapped application, at angularly spaced locations around the fracture situs of a bone 84, and excited in commutated sequence by means 85 interposed between the source of modulated-carrier signals and the separate lines of commutated supply to the respective transducers. Again, as in FIG. 7, provision is made at 75' in FIG. 8 for rate control and selective remote control, in a manner described for means 75 of FIG. 7.

It is a feature of the invention that once a space or spaces between bone-fragment surfaces has been closed to the point of an inability to sustain a standing-wave condition at the carrier frequency, the same low-frequency modulation can be delivered over a more widely diffused volume of propagation into the region of the fracture, on opposite longitudinal sides of the fracture. This can be achieved by various techniques, to be discussed in connection with FIGS. 9, 10 and 11.

In FIG. 9, a primary transducer 90 is supplied (via switching means 91) with modulated carrier for an initial space-closing phase of fracture repair, as for a period of several days or approximately a week. Thereafter, a remote control actuation at 92 may redirect the supply of modulated carrier to two outer transducers 93, 94, to the exclusion of transducer 90, thereby causing the continued acoustic propagation from transducers 93, 94 to become more spread and therefore rich in shear waves, thus favoring greater volumetric delivery of pulsed-carrier acoustic propagation. As shown, the transducers 93, 90, 94 are in longitudinal array, i.e. distributed along the longitudinal direction of a bone (not shown) toward which they non-invasively propagate.

In FIG. 10, successive transducers 95, 96 are in concentric array, and the central transducer 95 may be relied upon for standing-wave development and low-frequency signal demodulation in the initial phase of bone-fracture repair. Thereupon, as with means 91 of FIG. 9, the switching means 91' of FIG. 10 may be actuated to deliver modulated-carrier signals to the outer concentric annular transducer 96, to the exclusion of the central transducer 95, resulting in greater dispersion of shear-wave development in the volume of body tissue and/or fluids between the transducer and the region of fractured bone.

In the schematic representation of FIG. 11, it is indicated that a so-called modal converter 97, interposed between an acoustic transducer 98 and suitably coupled body tissue and/or fluids may be relied upon to develop even greater dispersion of acoustic shear-wave energy, if interposed between transducer 98 and the coupled body tissue and/or fluids. The resulting dispersion, preferably only in the second phase of fracture repair is schematically suggested by the solid-angle spread δ in FIG. 11.

The schematic diagram of FIG. 12 is a fragment of circuitry taken from FIG. 3 in order to show certain adjustable and adjustably variable features of apparatus serving one or more of the phases of bone-fracture repair. Thus, the modulated-carrier signal supplied to transducer 24 operates from the output of modulator 44' utilizing the low-frequency or osteogenic signal of generator 43' and the UHF carrier-signal output of generator 42'. For certain purposes, it is desirable to vary the frequency of the carrier, and such variation is schematically provided by suitable means 99, shown with various illustrative option and control-adjustment features. For example, in phase one of ultrahigh carrier frequency generation, in the megahertz range, suitably in the range 5 to 10 MHz, manual adjustment of means 99 suffices for such carrier-frequency selection, and for subsequent manual change to a lesser range, e.g., in the range 500 kHz to 5 MHz, after closure of fracture spaces and for the subsequent repair phase in which more diffused shear-wave propagation of the modulated carrier is desired.

Further in connection with the frequency-varying means 99 of FIG. 12, it is deemed desirable in certain cases to progressively and/or cyclically sweep the carrier frequency between upper and lower limits, such as 5 MHZ to 10 MHz in phase one, followed by reduced limits (e.g., 500 kHz to 5 MHz) in the subsequent phase of fracture healing. The selective availability of such limiting adjustments, including sweep rate, is indicated by legends at suitable controls suggested by labeled arrows. Specifically, frequency-varying means 99', operative upon the low-frequency signal generator 43', is shown by labeled arrows to be manually adjustable, and be controllable for sweep rate, and for upper and lower limits of swept low frequency.

To conclude the present description, it is well to summarize significant features of the invention, namely:

(a) An appreciation of the fact that bone-fracture repair can and should be addressed separately, for each of two phases, namely, a first phase of gap or space closure within the fracture, and an ensuing second phase of providing a volumetric environment rich in primary shear-waves, in broadened external envelopment of the fracture site.

(b) The use of a sufficiently elevated ultrahigh frequency acoustic carrier, modulated with a low-frequency signal of known osteogenic value, wherein the carrier frequency has a quarter-wave dimension in body tissue and/or fluids related to a minimum dimensional space attributable to the fracture, enables thus-modulated acoustic waves of the carrier to enter a waveguide situation between fracture-separated limits of one or more spaces within the fracture, wherein such spaces are large enough to permit a standing-wave phenomenon within a fracture-separated space, whereby to demodulate the carrier and thus secondarily and locally to establish a region of low-frequency shear-waves of known osteogenic value where most urgently needed in the first phase of fracture repair, namely, at and within the fracture site.

(c) At closure of the space or spaces within the fracture, other techniques are available for the second phase of fracture repair whereby to further enrich the volumetric surrounding environment of the fracture site, without necessarily resorting to continued flooding with the original low-frequency modulation of the same ultrahigh frequency carrier.

The nature of bone fractures in a living body is widely varying, and therefore acoustic bone-fracture repair techniques and parameter preferences will be subject to a range of values best determined by professional experience with numbers of fracture cases. Subject to this circumstance and the fact that experience to date has its limitations, it is nevertheless helpful to list presently recommended parameter values and ranges of parameter values, as follows:

1. The frequency of surgically non-invasive acoustic delivery into the body should be at least in approach to and in the low megahertz range (e.g. 20 kHz and above), calculated for standing-wave development within the fracture site, for propagation in body tissue and/or fluids. For an assumed minimum available fracture space of at least 0.04 mm attributable to the fracture, the carrier frequency should be at least 10 MHz.

2. The low-frequency signal to be used for at least the gap-closing first phase of fracture repair should be selected for known osteogenic value and osteogenic temperature rise in bone, suitably in a range of 0.01° C. to 2° C. At present, this leads to the recommended selection of pulsed modulation of the carrier wherein the pulse repetition rate is in the range 5 Hz to 10 KHz, preferably about one kilohertz; and with a duty cycle in the range of 5 percent to 90 percent.

3. Acoustic intensity at the fracture site is desirably less than 100 milliwatts/cm$^2$, and acoustic intensity at the transducer is recommended in the range 5 mW/cm$^2$ to 75 mW/cm$^2$, being preferably approximately 30 mW/cm$^2$.

4. The frequency of the carrier should be adjustably selectable, with provision for frequency sweeping between adjusted limits; for example, presently available transducers should be selected with at least a one to two octave frequency-response range.

5. The frequency of pulse modulation should be adjustably selectable, with provision for frequency sweeping between adjusted limits.

6. The transducer configuration should comprise one or more elements wherein the axis or axes of the elements may be of arbitrary relationship to and with each other, with provision for exciting multiple elements in a predetermined synchronized and repeatable time-varying manner.

Although the mechanisms involved in accelerating the healing of bone fractures through ultrasound stimulation as presently disclosed are not totally understood, it is believed that:

1. The standing-wave condition in body tissue and/or fluids will stimulate exposed nerve endings of the periosteum within the fracture site.

2. The "space" characterizing the fracture site is understood to be with or without body fluid, with or without tissue debris.

3. The multi-transducer configurations described herein are proposed to control the spatial, temporal, and frequency distribution of the acoustic energy in the region containing the fracture complex.

4. There are at least five unique features characterizing this invention, namely:

(a) The nominal value of the carrier frequency is sufficient to set up a standing-wave condition in the space characterizing the fracture state, as well as to stimulate the exposed nerve endings of the periosteum.

(b) A standing-wave condition within the fracture space is demodulated as a shear wave at the pulse repetition frequency.

(c) The acoustic intensity at the fracture site exceeds the biological threshold to provoke biological regulatory feedback mechanisms.

(d) The pulse repetition period is less than the relaxation times of the significant regulatory healing mechanisms.

(e) Multi-element array configurations, pulse modulation and carrier frequency control, and temporal control, permit matching the spatial frequency and temporal distribution of acoustic energy to the complex structure of a particular fracture, thereby to optimize the healing process.

The acoustic intensity at the fracture site refers to the Spatial Average Temporal Average (SATA) intensity as defined by the AIUM-NEMA 1981 Standard.

We claim:

1. The method of surgically non-invasively using low-frequency acoustic energy to accelerate repair of a bone fracture, wherein the fracture includes a space between confronting surface portions of the fracture; said method comprising the step of non-invasively and transcutaneously delivering ultrahigh-frequency acoustic carrier-frequency energy to body tissue and/or fluids adjacent at least a portion of the fracture and at a wavelength to establish a vibrating standing-wave condition in the space wherein said space is at least of quarter wavelength extent.

2. The method of claim 1, including the additional step of establishing a therapeutic condition of osteogenic value to bone-tissue within and on both sides of the space by modulating said ultrahigh frequency with a low-frequency signal of osteogenic value, and utilizing the standing-wave condition for local demodulation to said low-frequency signal.

3. The method of claim 2, wherein the modulating low frequency signal has a duty cycle and pulse amplitude that cause an osteogenic temperature rise in bone.

4. The method of claim 3, in which the temperature rise is at least 0.01° C.

5. The method of claim 4, in which the temperature rise is less than 2° C.

6. The method of surgically non-invasively using low-frequency acoustic energy to accelerate repair of a bone fracture, wherein said method comprises the steps of:

(a) selecting an electro-acoustic transducer for direct application of ultrahigh-frequency energy to the skin;

(b) placing and holding the transducer at a region of acoustic transcutaneous coupling to body tissue and/or fluids adjacent at least a portion of the fracture;

(c) exciting the transducer with a low-frequency modulation of an ultrahigh-frequency carrier, wherein the carrier frequency is in a range between 20 kHz and 10 MHz, said modulation frequency having a range between about 5 Hz and 10 kHz; wherein the fracture includes a space between adjacent portions of the fractured bone wherein the space is at least one-quarter wavelength at the carrier frequency, the method further including establishing a standing-wave condition within the fracture, resulting in a demodulated low-frequency acoustic shear-wave signal of known osteogenic value local to and within the fracture; and (d) maintaining such excitation of the transducer at an intensity for acoustic-energy coupling to body tissue and/or fluids such that said intensity is less than 100 milliwatts/cm$^2$ at the fracture, the maintaining of such excitation being for a predetermined period of time per day.

7. The method of claim 6, wherein said predetermined period is at least five minutes per day.

8. The method of claim 6, wherein said predetermined period is less than 4 hours per day.

9. The method of claim 6, wherein the period of step (d) is approximately 20 minutes at least once per day.

10. The method of claim 6, wherein the period of step (d) is approximately 20 minutes at least twice per day.

11. The method of claim 6,, wherein said modulation frequency is varied between limits within said modulating-frequency range.

12. The method of claim 11, wherein the variation of said modulating frequency is a continuous variation.

13. The method of claim 12, wherein the variation of said modulation is cyclic and has a period of approximately one minute.

14. The method of claim 12, wherein the variation of said modulation is cyclic and has a period of at least one minute.

15. The method of claim 11, wherein the variation of said modulation is cyclic and has a period of approximately one minute.

16. The method of claim 11, wherein the variation of said modulation is cyclic and has a period of at least one minute.

17. The method of claim 6, wherein the placing and holding of step (b) includes angularly displacing an orientation of the transducer with respect to the region of acoustic transcutaneous coupling, the angular displacement being at a rate of at least one-half degree per second.

18. The method of claim 17, in which said displacement is between predetermined limits and with a recurring periodicity of approximately one minute.

19. The method of claim 6, wherein the modulated carrier of step (c) comprises a pulsed modulation having a duty cycle in a range of 5 percent to 90 percent.

20. The method of claim 6, wherein the selection and placement of steps (a) and (b) place a first selected transducer transcutaneously coupled to body tissue and/or fluids on one side of the bone fracture, and also place a second selected transducer transcutaneously coupled to body tissue and/or fluids on the other side of the bone fracture; and wherein the excitation of step (c) is applied to each of said transducers.

21. The method of claim 20, wherein each of said excitations is pulse modulated in time-interlaced relation.

22. The method of claim 6, wherein the selection and placement of steps (a) and (b) place and orient a first selected transducer transcutaneously coupled to body tissue and/or fluids at one lateral aspect of the bone fracture, and in which said first transducer is one of a plurality of similarly coupled transducers in spaced relation to each other and in oriented aspects which are directed at the fracture; and wherein the excitation of step (c) is applied to each of said transducers.

23. The method of claim 22, in which said plurality of transducers is arrayed in longitudinally spaced relation generally parallel to the fractured bone.

24. The method of claim 23, in which the transducers of said plurality of transducers are sequentially excited pursuant to step (c).

25. The method of claim 22, in which said plurality of transducers is arrayed in generally circumferentially spaced relation around the fracture.

26. The method of claim 25, in which the transducers of said plurality of transducers are sequentially excited pursuant to step (c).

27. Apparatus for use of low-frequency sound to accelerate repair of a bone fracture, said apparatus comprising electroacoustic transducer means having a frontal-surface area centered on a longitudinal axis of directional propagation, said transducer means being adapted for non-invasive direct externally coupled application to skin and for subcutaneous coupling to body tissue and/or fluids adjacent a fracture, wherein the fracture has fracture-spaced confronting walls, and generator means for exciting said transducer means with an electrical signal, wherein said signal further includes:

(i) an ultrahigh acoustic carrier frequency in a range between 20 kHz and 10 MHz, for acoustic propagation in body tissue and/or fluids, said acoustic propagation having (a) a primary directional lobe centered on and primarily in the longitudinal direction of said axis, and having (b) within a volume surrounding and outside said lobe, a relatively wide region that is rich in primary shear waves;

(ii) a low-frequency bone-therapy modulation of said carrier frequency in a range of 5 Hz to 10 kHz; and (iii) an acoustic intensity less than 100 milliwatts/cm$^2$ at the fracture;

thereby (a) to permit directional delivery of modulated-carrier acoustic energy via said primary directional lobe to at least a portion of the fracture and (b) to utilize the fracture-spaced confronting walls as a wave guide for establishing a standing-wave condition of the carrier frequency within at least a portion of the fracture, so that the standing-wave condition can provide local demodulation of the modulated carrier, with secondary shear-wave development of a low-frequency bone-therapy acoustic signal local to and within the fracture, and (c) to flood with primary shear-waves body tissue and/or body-fluid external to the fracture.

28. The apparatus of claim 27, in which said low-frequency modulation is a pulsed modulation.

29. The apparatus of claim 28, in which said pulsed modulation has a duty cycle in a range of 5 percent to 90 percent.

30. The apparatus of claim 27, in which acoustic intensity at said transducer means is in a range 5 mW/cm$^2$ to 75 mW/cm$^2$.

31. The apparatus of claim 30, in which acoustic intensity at said transducer means is approximately 30 mW/cm$^2$.

32. The apparatus of claim 27, in which the frequency of said carrier is at least one megahertz.

33. The apparatus of claim 27, further including means for periodically sweeping the modulating frequency of said carrier between predetermined upper and lower limiting frequencies within said 5 Hz to 10 kHz range.

34. The apparatus of claim 27, further including means for periodically sweeping the frequency of the carrier between predetermined upper and lower limiting frequencies within said 25 kHz to 10 MHz range.

35. The apparatus of claim 34, in which said last mentioned range is between 2.5 MHz and 10 MHz.

36. The apparatus of claim 27, in which said transducer means is one of a plurality of transducers all of which are adapted to be in similar but spaced direct coupling to body tissue and/or fluids with their respective longitudinal axes of propagation directed to one or more portions of the fracture.

37. The apparatus of claim 36, in which said generator means has separate output connections to at least two of said transducers, and wherein said low,frequency modulation is a pulsed modulation, with the pulsed modulation delivered to one of said transducers in time-interlace with the pulsed modulation delivered to a second of said transducers.

38. The apparatus of claim 35, in which said generator means has separate output connections to a plurality of said transducers, and wherein said low-frequency modulation is a pulsed modulation, with the pulsed modulation delivered to each transducer in time-interlace with the pulsed modulation delivered to other transducers of said plurality.

39. The apparatus of claim 27, further including a mounting structure for said transducer means, said mounting structure being adapted to be mounted to an afflicted body part of a patient.

40. The apparatus of claim 39, in which said mounting structure includes means for adjustably movable positioning of said transducer means with respect to the body part.

41. The apparatus of claim 40, in which said transducer means includes a plurality of like transducers and said mounting structure includes means for selectively mounting the plurality of like transducers wherein the transducers are adapted to be directly coupled in similar but spaced relation to body tissue and/or fluids, and have longitudinal axes of propagation directed to one or more portions of the fracture.

42. The apparatus of claim 27, in which said electroacoustic transducer means includes means for modal conversion of the directional propagation of said transducer means.

43. The apparatus of claim 42, further including selectively operable means for selectively operating modal conversion of the directional propagation of said transducer means.

44. The apparatus of claim 27, in which said transducer means includes a first transducer component having said frontal-surface area, and in which said transducer means further includes a second transducer component having a separate frontal-surface area to provide enhanced richness of primary shear-wave propagation when said second transducer component is energized.

45. The apparatus of claim 44, in which the frontal-surface of said first transducer component is circular, and in which the frontal surface of said second transducer component is at least one annulus which surrounds said first transducer component.

46. The apparatus of claim 44, in which said second transducer component comprises one or more spaced frontal-surface areas adjacent to said first transducer component.

47. The apparatus of claim 44, in which the frontal surface of said second transducer component comprises two or more spaced frontal-surface areas adjacent to said first transducer component and symmetrically disposed on laterally opposite sides of said first transducer component.

* * * * *